(12) United States Patent
Bhavaraju et al.

(10) Patent No.: US 10,369,283 B2
(45) Date of Patent: Aug. 6, 2019

(54) SYSTEMS AND METHODS FOR MANAGING GLYCEMIC VARIABILITY

(71) Applicant: DexCom, Inc., San Diego, CA (US)

(72) Inventors: Naresh C. Bhavaraju, San Diego, CA (US); Arturo Garcia, Chula Vista, CA (US); Phil Mayou, San Diego, CA (US); Thomas A. Peyser, Menlo Park, CA (US); Apurv Ullas Kamath, San Diego, CA (US); Aarthi Mahalingam, San Diego, CA (US); Kevin Sayer, Carlsbad, CA (US); Thomas Hall, San Diego, CA (US); Michael Robert Mensinger, San Diego, CA (US); Hari Hampapuram, San Diego, CA (US); David Price, Carlsbad, CA (US); Jorge Valdes, San Diego, CA (US); Murrad Kazalbash, Placentia, CA (US)

(73) Assignee: DexCom, Inc., San Diego, CA (US)

(*) Notice: Subject to any disclaimer, the term of this patent is extended or adjusted under 35 U.S.C. 154(b) by 718 days.

(21) Appl. No.: 14/065,847

(22) Filed: Oct. 29, 2013

(65) Prior Publication Data

US 2014/0128837 A1    May 8, 2014

Related U.S. Application Data

(63) Continuation of application No. 13/790,281, filed on Mar. 8, 2013, now abandoned.
(Continued)

(51) Int. Cl.
*G01N 33/48* (2006.01)
*A61M 5/172* (2006.01)
(Continued)

(52) U.S. Cl.
CPC .......... *A61M 5/1723* (2013.01); *A61M 5/142* (2013.01); *G01N 33/49* (2013.01);
(Continued)

(58) Field of Classification Search
None
See application file for complete search history.

(56) References Cited

U.S. PATENT DOCUMENTS 8,538,703 B2   9/2013  Kovatchev et al.
2004/0091424 A1   5/2004  Asano et al.
(Continued)

FOREIGN PATENT DOCUMENTS

EP   2006786 A1   12/2008
EP   2400415 A2   12/2011
(Continued)

OTHER PUBLICATIONS

Czerwonkiuk et al., 2011, J. Diabetes Science and Technology 5(2):447-451. GluCulator: A glycemic variability calculation tool for continuous glucose monitoring data.
(Continued)

*Primary Examiner* — Larry D Riggs, II
(74) *Attorney, Agent, or Firm* — Knobbe Martens Olson & Bear, LLP

(57) ABSTRACT

Methods and apparatus, including computer program products, are provided for processing analyte data. In some example implementations, a method may include generating glucose sensor data indicative of a host's glucose concentration using a glucose sensor; calculating a glycemic variability index (GVI) value based on the glucose sensor data; and providing output to a user responsive to the calculated glycemic variability index value. The GVI may be a ratio of a length of a line representative of the sensor data and an ideal length of the line. Related systems, methods, and articles of manufacture are also disclosed.

20 Claims, 11 Drawing Sheets

Related U.S. Application Data

(60) Provisional application No. 61/723,642, filed on Nov. 7, 2012.

(51) Int. Cl.
  *A61M 5/142* (2006.01)
  *G01N 33/49* (2006.01)
  *G06F 19/00* (2018.01)
  *G16H 40/63* (2018.01)
  *G16H 50/30* (2018.01)

(52) U.S. Cl.
  CPC .............. *G06F 19/00* (2013.01); *G06F 19/30* (2013.01); *G06F 19/3418* (2013.01); *G16H 40/63* (2018.01); *G16H 50/30* (2018.01)

(56) References Cited

U.S. PATENT DOCUMENTS

| | | | |
|---|---|---|---|
| 2007/0012322 A1* | 1/2007 | Ragg | A61M 5/427 128/898 |
| 2010/0022988 A1 | 1/2010 | Wochner | |
| 2010/0094251 A1 | 4/2010 | Estes | |
| 2010/0331654 A1 | 12/2010 | Jerdonek et al. | |
| 2011/0004085 A1 | 1/2011 | Mensinger et al. | |
| 2011/0205064 A1 | 8/2011 | Strachan et al. | |
| 2011/0205065 A1 | 8/2011 | Strachan et al. | |
| 2011/0245634 A1 | 10/2011 | Ray et al. | |
| 2012/0172694 A1 | 7/2012 | Desborough et al. | |
| 2013/0332181 A1 | 12/2013 | Schmidt et al. | |
| 2013/0332182 A1 | 12/2013 | Schmidt et al. | |
| 2015/0135118 A1* | 5/2015 | Grubstein | A61B 5/684 715/771 |

FOREIGN PATENT DOCUMENTS

| | | |
|---|---|---|
| EP | 2400416 A2 | 12/2011 |
| WO | WO 2011/091238 | 7/2011 |
| WO | WO 2011/106029 | 9/2011 |
| WO | WO 2011/123775 | 10/2011 |

OTHER PUBLICATIONS

Marling et al., 2011, J. Diabetes Science and Technology 5(4):871-878. Characterizing blood glucose variability using new metrics with continuous glucose monitoring.

Rodbard et al., 2009, Diabetes Technology and Therapeutics 11(9):551-565. New and improved methods to characterize glucemic variability using continuous glucose monitoring.

Sieglaar et al., Diabetes Care 34:855-857 (2011): A decrease in glucose variability does not reduce cardiovascular event rates in type 2 diabetic patients after acute myocard.

* cited by examiner

SYSTEMS AND METHODS FOR MANAGING GLYCEMIC VARIABILITY

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 13/790,281, filed on Mar. 8, 2013, which claims the benefit of U.S. Provisional Application No. 61/723,642, filed on Nov. 7, 2012, the disclosure of which is hereby expressly incorporated by reference in its entirety and is hereby expressly made a portion of this application.

FIELD OF THE INVENTION

The present disclosure generally relates to data processing of glucose data of a host.

BACKGROUND OF THE INVENTION

Diabetes mellitus is a disorder in which the pancreas cannot create sufficient insulin, such as in the case of Type I diabetes and/or in which insulin is not effective, such as Type 2 diabetes. In a diabetic state, a victim suffers from high blood sugar, which causes an array of physiological derangements, such as kidney failure, skin ulcers, or bleeding into the vitreous of the eye, associated with the deterioration of small blood vessels. A hypoglycemic reaction, such as low blood sugar, may be induced by an inadvertent overdose of insulin, or after a normal dose of insulin or glucose-lowering agent accompanied by extraordinary exercise or insufficient food intake.

A diabetic person may carry a self-monitoring blood glucose (SMBG) monitor, which typically requires uncomfortable finger pricking methods. Due to the lack of comfort and convenience, a diabetic typically measures his or her glucose level only two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is higher or lower based on conventional methods.

Consequently, a variety of non-invasive, transdermal (e.g., transcutaneous) and/or implantable electrochemical sensors are being developed for continuously detecting and/or quantifying blood glucose values. These devices and other types of devices generally transmit raw or minimally processed data for subsequent analysis at a remote device, which can include a display, to allow presentation of information to a user hosting the sensor.

SUMMARY OF THE INVENTION

The various embodiments and implementations of the present systems and methods have several features, no single one of which is solely responsible for their desirable attributes. Without limiting the scope of the present embodiments and implementations as expressed by the claims that follow, their more prominent features now will be discussed briefly. After considering this discussion, and particularly after reading the section entitled "Detailed Description," one will understand how the features of the present embodiments provide the advantages described herein.

Methods and apparatus, including computer program products, are provided for processing analyte data. In a first aspect, a computer-implemented method is provided. The method comprises generating glucose sensor data indicative of a host's glucose concentration using a glucose sensor; calculating a glycemic variability index (GVI) value based on the glucose sensor data; and providing output to a user responsive to the calculated glycemic variability index value.

In an implementation of the first aspect, which is generally applicable, particularly with any other implementation of the first aspect, the GVI is defined as GVI=L/Lo, wherein L is a length of a line representative of the host's glucose concentration over a period of time and Lo is an ideal line length for the given period of time.

In another implementation of the first aspect, which is generally applicable, particularly with any other implementation of the first aspect, the first aspect further comprises calculating a Patient Glycemic Status (PGS), wherein PGS is defined as PGS=GVI*MG*(1−PTIR)+Penalty, wherein MG is a mean glucose value of the sensor data, PTIR is a percentage of time the sensor data is within a predefined range of glucose concentration values, and the Penalty is a non-linear hyperbolic function that asymptotes with a predetermined number of determined episodes of severe hypoglycemia within a predetermined amount of time. The predefined range of glucose concentration values can be between about 80 mg/dL and about 180 mg/dL.

In another implementation of the first aspect, which is generally applicable, particularly with any other implementation of the first aspect, the providing output is responsive to the GVI calculation and the PSG calculation.

In another implementation of the first aspect, which is generally applicable, particularly with any other implementation of the first aspect, the providing output comprises generating a report to a user, wherein the report includes a calculated GVI numerical value.

In another implementation of the first aspect, which is generally applicable, particularly with any other implementation of the first aspect, the providing output comprises triggering an alert to a user when the GVI exceeds a predetermined threshold, wherein the alert is one or more of an audible alert, visual alert and tactile alert.

In another implementation of the first aspect, which is generally applicable, particularly with any other implementation of the first aspect, the calculating is automatically performed periodically on a defined window of time of sensor data.

In another implementation of the first aspect, which is generally applicable, particularly with any other implementation of the first aspect, the calculating comprising calculating a plurality of GVI values based on the sensor data, wherein each of the GVI values is based on a different period of time of the sensor data.

In another implementation of the first aspect, which is generally applicable, particularly with any other implementation of the first aspect, the method is performed by a processor executing code embodied in a non-transitory computer-readable medium.

In a second aspect, a non-transitory computer-readable medium including code which when executed by at least one processor provides operations is provided. The operations comprise: providing a scoring map that coverts glucose values to a clinical relevance score; converting glucose values generated using a continuous glucose sensor from units of glucose concentration to clinical relevance scores using the scoring map; applying a statistical algorithm to the clinical relevance scores to generate a processed clinical relevance score; and outputting information based on the processed clinical relevance score to a user interface of an electronic device.

In an implementation of the second aspect, which is generally applicable, particularly with any other implementation of the second aspect, the scoring map is embodied as one or more mathematical equations.

In another implementation of the second aspect, which is generally applicable, particularly with any other implementation of the second aspect, the scoring map comprises an above target coordinate space and a below target coordinate space.

In another implementation of the second aspect, which is generally applicable, particularly with any other implementation of the second aspect, the scale of the clinical relevance score is linear and the scale of the glucose concentration is non-linear.

In another implementation of the second aspect, which is generally applicable, particularly with any other implementation of the second aspect, the statistical algorithm comprises one or more of a sum, mean, average and standard deviation of the clinical relevance scores.

In another implementation of the second aspect, which is generally applicable, particularly with any other implementation of the second aspect, the outputted information comprises one or more of a numerical clinical relevance score and a graph of the clinical relevance scores over time.

In a third aspect, a system is provided. The system comprises: at least one processor; at least one memory including code which when executed by the at least one processor provides operations comprising analyzing glucose data generated by a continuous glucose sensor over a time period, identifying an event based on the analyzing, and outputting information to a user via a user interface of the system, the information based on the identified event.

In another implementation of the third aspect, which is generally applicable, particularly with any other implementation of the third aspect, the event is a missed meal event, and wherein the information includes a prompt for a user to enter meal information.

In another implementation of the third aspect, which is generally applicable, particularly with any other implementation of the third aspect, the event is a missed insulin administration event, and wherein the identifying includes monitoring whether a rate of change of the host's measured glucose levels exceeds a threshold for a predetermined period of time.

In another implementation of the third aspect, which is generally applicable, particularly with any other implementation of the third aspect, the information comprises an indication of glucose control associated with the wear of an insulin infusion pump.

In another implementation of the third aspect, which is generally applicable, particularly with any other implementation of the third aspect, the information comprises a message indicating a percentage of measured glucose values falling within a target range over a predetermined time period.

Figure 1:
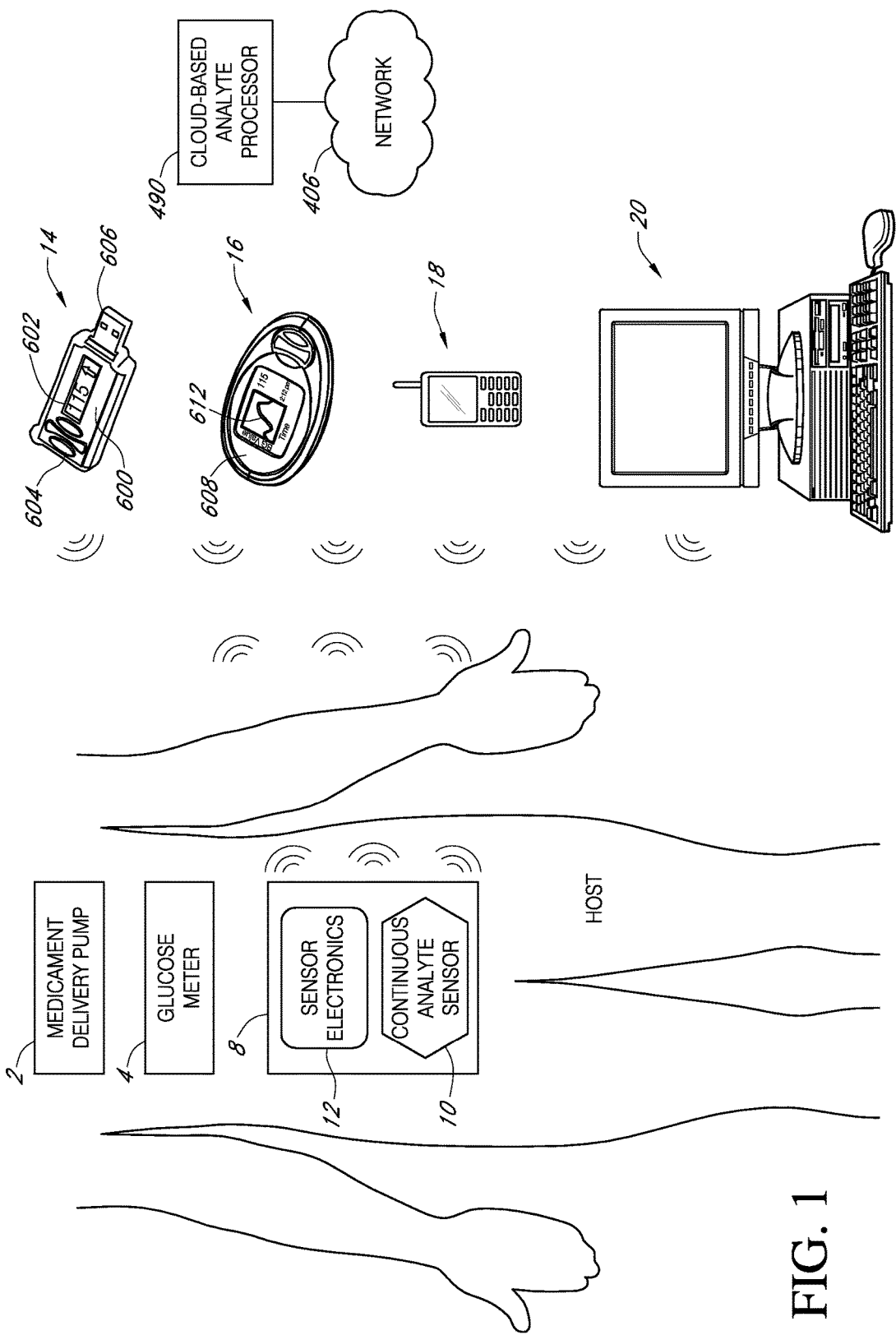
FIG. 1 depicts a diagram illustrating a continuous analyte sensor system including a sensor electronics module in accordance with some exemplary implementations.

Like labels are used to refer to same or similar items in the drawings.

DETAILED DESCRIPTION

FIG. 1 depicts an example system 100, in accordance with some exemplary implementations. The system 100 includes a continuous analyte sensor system 8 including a sensor electronics module 12 and a continuous analyte sensor 10. The system 100 may include other devices and/or sensors, such as medicament delivery pump 2 and glucose meter 4. The continuous analyte sensor 10 may be physically connected to sensor electronics module 12 and may be integral with (e.g., non-releasably attached to) or releasably attachable to the continuous analyte sensor 10. The sensor electronics module 12, medicament delivery pump 2, and/or glucose meter 4 may couple with one or more devices, such as display devices 14, 16, 18, and/or 20.

In some exemplary implementations, the system 100 may include a cloud-based analyte processor 490 configured to analyze analyte data (and/or other patient related data) provided via network 406 (e.g., via wired, wireless, or a combination thereof) from sensor system 8 and other devices, such as display devices 14-20 and the like, associated with the host (also referred to as a patient) and generate reports providing high-level information, such as statistics, regarding the measured analyte over a certain time frame. Although the example implementation described with respect to FIG. 1 refers to analyte data being received by analyte processor 490, other types of data processed and raw data may be received as well.

In some exemplary implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor. An example implementation of the sensor electronics module 12 is described further below with respect to FIG. 2.

The sensor electronics module 12 may, as noted, couple (e.g., wirelessly and the like) with one or more devices, such as display devices 14, 16, 18, and/or 20. The display devices 14, 16, 18, and/or 20 may be configured for presenting (and/or alarming) information, such as sensor information transmitted by the sensor electronics module 12 for display at the display devices 14, 16, 18, and/or 20.

The display devices may include a relatively small, key fob-like display device 14, a relatively large, hand-held display device 16, a smart phone or tablet computing device 18, a computer workstation 20, and/or any other user equipment configured to at least present information (e.g., a medicament delivery information, discrete self-monitoring glucose readings, heart rate monitor, caloric intake monitor, and the like).

In some exemplary implementations, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device) and may be configured to display certain types of displayable sensor information, such as a numerical value and an arrow.

In some exemplary implementations, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some exemplary implementations, the continuous analyte sensor 10 may analyze a plurality of intermittent blood samples, although other analytes may be used as well.

In some exemplary implementations, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

In some implementations, the system 100 includes a DexCom G4® Platinum continuous analyte monitor commercially available from DexCom, Inc., for continuously monitoring a host's glucose levels.

Although the description herein refers to some implementations that include a continuous analyte sensor 10 comprising a glucose sensor, the continuous analyte sensor 10 may comprises other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, Acetyl Co A, triglycerides, fatty acids, intermediaries in the citric acid cycle, choline, insulin, cortisol, testosterone, and the like.

Figure 2:
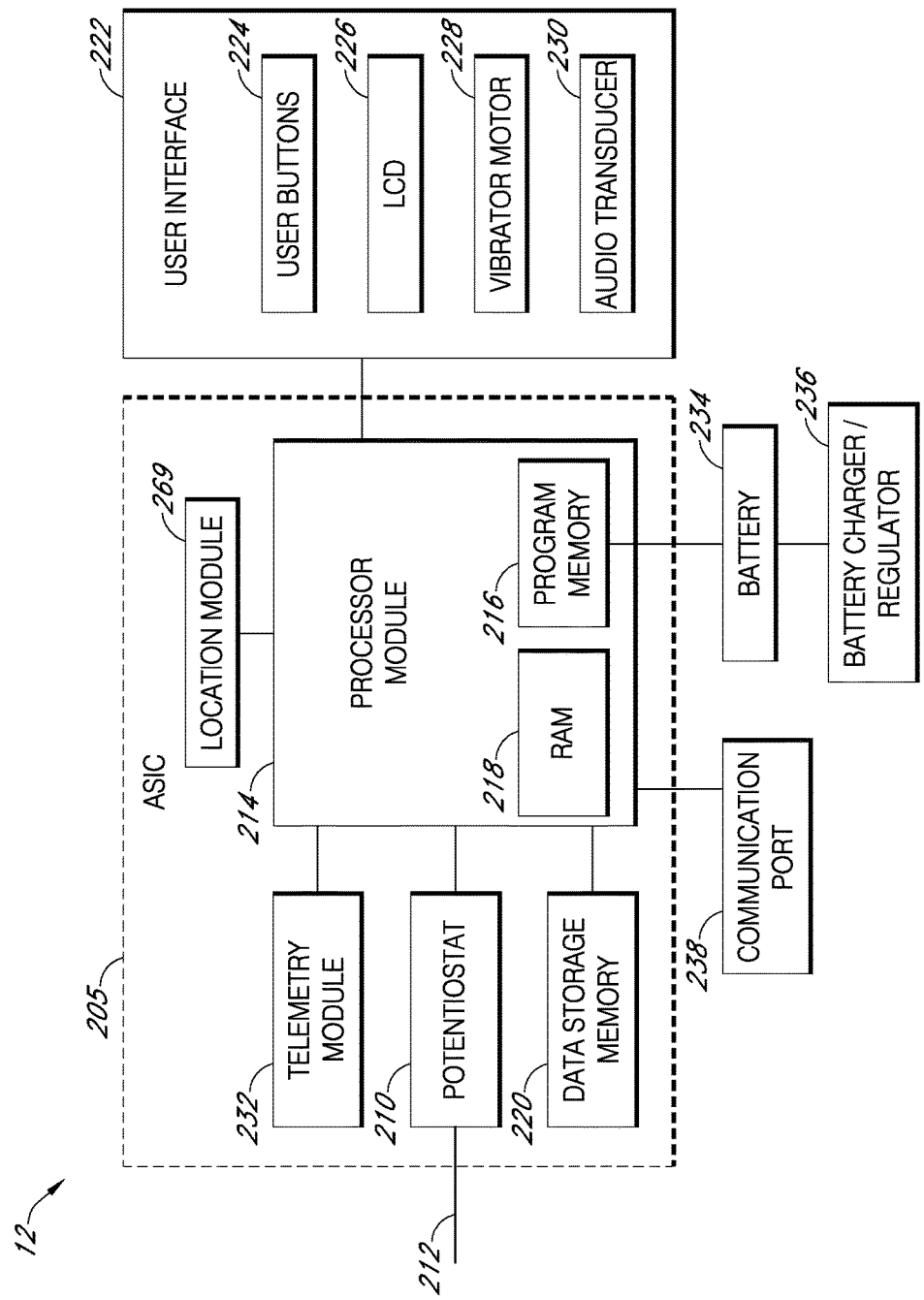
FIG. 2 depicts a block diagram illustrating the sensor electronics module in accordance with some exemplary implementations.

FIG. 2 depicts an example of a sensor electronics module 12, in accordance with some exemplary implementations. The sensor electronics module 12 may include sensor electronics that are configured to process sensor information, such as sensor data, and generate transformed sensor data and displayable sensor information. For example, the sensor electronics module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration information, sensor diagnostic information, location information (which may be provided by a location module 269 providing location information, such as global positioning system information), alarm/alert information, calibration information, smoothing and/or filtering algorithms of sensor data, and/or the like.

In some exemplary implementations, the sensor electronics module 12 may be configured to calibrate the sensor data, and the data storage memory 220 may store the calibrated sensor data points as transformed sensor data. Moreover, the sensor electronics module 12 may be configured, in some exemplary implementations, to wirelessly receive calibration information from a display device, such as devices 14, 16, 18, and/or 20, to enable calibration of the sensor data from sensor 12 and data line 212. Furthermore, the sensor electronics module 12 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms.

In some exemplary implementations, the sensor electronics module 12 may comprise an application-specific integrated circuit (ASIC) 205 coupled to a user interface 122. The ASIC 205 may further include a potentiostat 210, a telemetry module 232 for transmitting data from the sensor electronics module 12 to one or more devices, such devices 14, 16, 18, and/or 20, and/or other components for signal processing and data storage (e.g., processor module 214 and data store 220). Although FIG. 2 depicts ASIC 205, other types of circuitry may be used as well, including field programmable gate arrays (FPGA), one or more microprocessors configured to provide some (if not all of) the processing performed by the sensor electronics module 12, analog circuitry, digital circuitry, or a combination thereof.

In the example depicted at FIG. 2, the potentiostat 210 is coupled to a continuous analyte sensor 10, such as a glucose sensor, via data line 212 to receive sensor data from the analyte. The potentiostat 210 may also provide via data line 212 a voltage to the continuous analyte sensor 10 to bias the sensor for measurement of a value (e.g., a current and the like) indicative of the analyte concentration in a host (also referred to as the analog portion of the sensor). The potentiostat 210 may have one or more channels (and corresponding one or more data lines 212), depending on the number of working electrodes at the continuous analyte sensor 10.

In some exemplary implementations, the potentiostat 210 may include a resistor that translates a current value from the sensor 10 into a voltage value, while in some exemplary implementations, a current-to-frequency converter may also be configured to integrate continuously a measured current value from the sensor 10 using, for example, a charge-counting device. In some exemplary implementations, an analog-to-digital converter may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics module 12 and one or more other devices, such as display devices, processors, network access devices, and the like. A variety of wireless radio technologies that can be implemented in the telemetry module 232 include Bluetooth, Bluetooth Low-Energy, the ANT protocol, NFC (near field communications), ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some exemplary implementations, the telemetry module 232 comprises a Bluetooth chip, although the Bluetooth technology may also be implemented in a combination of the telemetry module 232 and the processor module 214.

The processor module 214 may control the processing performed by the sensor electronics module 12. For example, the processor module 214 may be configured to process data (e.g., counts), from the sensor, filter the data, calibrate the data, perform fail-safe checking, and/or the like.

In some exemplary implementations, the processor module 214 may comprise a digital filter, such as for example an infinite impulse response (IIR) or a finite impulse response (FIR) filter. This digital filter may smooth a raw data stream received from sensor 10, data line 212 and potentiostat 210 (e.g., after the analog-to-digital conversion of the sensor data). Generally, digital filters are programmed to filter data sampled at a predetermined time interval (also referred to as a sample rate). In some exemplary implementations, such as when the potentiostat 210 is configured to measure the analyte (e.g., glucose and the like) at discrete time intervals, these time intervals determine the sampling rate of the digital filter. In some exemplary implementations, the potentiostat 210 is configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter.

The processor module 214 may further include a data generator configured to generate data packages for transmission to devices, such as the display devices 14, 16, 18, and/or 20. Furthermore, the processor module 215 may generate data packets for transmission to these outside sources via telemetry module 232. In some exemplary implementations, the data packages may, as noted, be customizable for each display device, and/or may include any available data, such as a time stamp, displayable sensor information, transformed sensor data, an identifier code for the sensor and/or sensor electronics module, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics module 12 and/or charge the batteries 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/functions described herein. For example, the program code may configure processor module 214 to process data streams or counts, filter, calibrate, perform fail-safe checking, and the like.

The memory 218 may also be used to store information. For example, the processor module 214 including memory 218 may be used as the system's cache memory, where temporary storage is provided for recent sensor data received from data line 212 and potentiostat 210. In some exemplary implementations, the memory may comprise memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some exemplary implementations, the data storage memory 220 stores one or more days of continuous analyte sensor data. For example, the data storage memory may store 1, 3, 4, 5, 6, 7, 8, 9, 10, 11, 12, 13, 14, 15, 20, and/or 30 (or more days) of continuous analyte sensor data received from sensor 10 via data line 212. The stored sensor information may include one or more of the following: a time stamp, raw sensor data (one or more raw analyte concentration values), calibrated data, filtered data, transformed sensor data, and/or any other displayable sensor information.

The user interface 222 may include a variety of interfaces, such as one or more buttons 224, a liquid crystal display (LCD) 226, a vibrator 228, an audio transducer (e.g., speaker) 230, a backlight, and/or the like. The components that comprise the user interface 222 may provide controls to interact with the user (e.g., the host). One or more buttons 224 may allow, for example, toggle, menu selection, option selection, status selection, yes/no response to on-screen questions, a "turn off" function (e.g., for an alarm), a "snooze" function (e.g., for an alarm), a reset, and/or the like. The LCD 226 may provide the user with, for example, visual data output. The audio transducer 230 (e.g., speaker) may provide audible signals in response to triggering of certain alerts, such as present and/or predicted hyperglycemic and hypoglycemic conditions. In some exemplary implementations, audible signals may be differentiated by tone, volume, duty cycle, pattern, duration, and/or the like. In some exemplary implementations, the audible signal may be configured to be silenced (e.g., snoozed or turned off) by pressing one or more buttons 224 on the sensor electronics module and/or by signaling the sensor electronics module using a button or selection on a display device (e.g., key fob, cell phone, and/or the like).

Although audio and vibratory alarms are described with respect to FIG. 2, other alarming mechanisms may be used as well. For example, in some exemplary implementations, a tactile alarm is provided including a poking mechanism configured to "poke" the patient in response to one or more alarm conditions.

The battery 234 may be operatively connected to the processor module 214 (and possibly other components of the sensor electronics module 12) and provide the necessary power for the sensor electronics module 12. In some exemplary implementations, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some exemplary implementations, the battery is rechargeable. In some exemplary implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some exemplary implementations, a battery regulator (or balancer) 236 regulates the recharging process by bleeding off excess charge current to allow all cells or batteries in the sensor electronics module to be fully charged without overcharging other cells or batteries. In some exemplary implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a personal computer (PC) communication (com) port can be provided to enable communication with systems that are separate from, or integral with, the sensor electronics module. The communication port, for example, may comprise a serial (e.g., universal serial bus or "USB") communication port, to communicate with another computer system (e.g., PC, personal digital assistant or "PDA," server, or the like). The communication port may also be coupled to a wireless transceiver to allow wireless communications as well. In some exemplary implementations, the sensor electronics module 12 is able to transmit historical data to a PC or other computing device (e.g., an analyte processor as disclosed herein) for retrospective analysis by a patient and/or physician.

In some continuous analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics module 12 may be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Although separate data storage and program memories are shown in FIG. 2, a variety of configurations may be used as well. For example, one or more memories may be used to provide storage space to support data processing and storage requirements at sensor electronic module 12.

Figure 3:
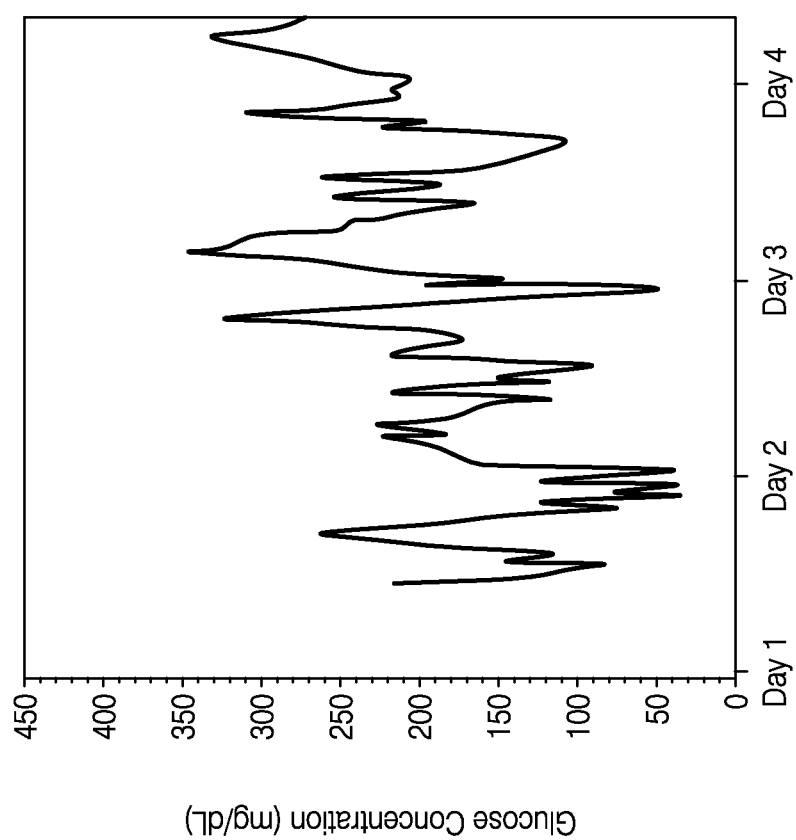
FIG. 3 is a graph of glucose concentration data plotted over several days indicative of poor glucose control in accordance with some exemplary implementations.

Some implementations evaluate a host's glycemic variability over time and provide output responsive to the evaluation. Variability of a host's glucose concentration is recognized as a risk factor for long-term complications and a factor for severe hypoglycemia. Further, glycemic variability has been associated with physical and emotional distress. FIG. 3 is a graph illustrating glucose readings of a user that is believed to be exhibiting high glucose variability, as it can be seen from the graph that the user's glucose levels are rapidly swinging between high and low glucose levels.

Figure 4:
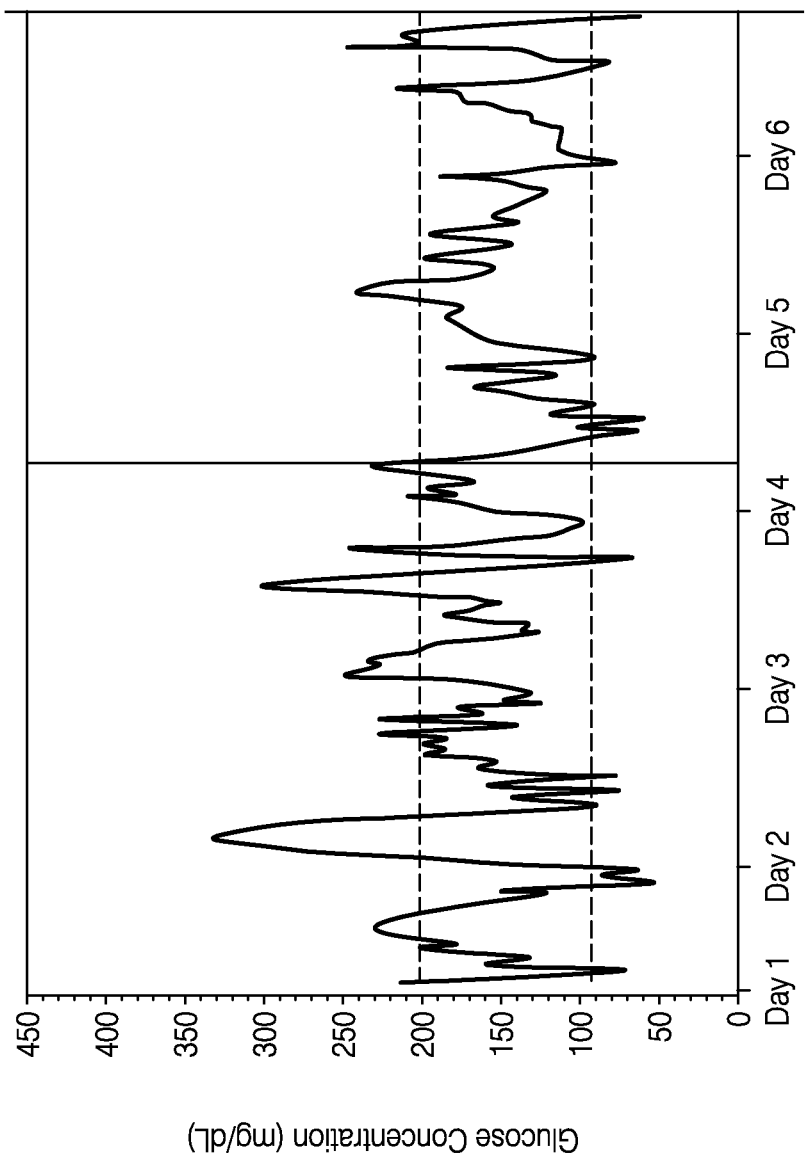
FIG. 4 is a graph of glucose concentration data plotted over several days indicative of improving glucose control in accordance with some exemplary implementations.

It is believed that a user that can continuously monitor his or her glucose levels can reduce glycemic variability. FIG. 4 is a graph of a glucose concentration of a user as measured using the DexCom STS® continuous glucose monitoring system over six days. The DexCom STS® continuous glucose monitoring system is commercially available from DexCom, Inc. FIG. 4 illustrates that this user's glucose concentration varied significantly more over the first three days than the following three days. It is believed that the reduction in glucose variability is due to the user being able to monitor his or her glucose concentration in real time using the DexCom STS system, thereby being able to more effectively manage his or her condition.

Glycemic Variability Index

In some implementations, a computing system, such as any of the computing systems described herein, calculates a Glycemic Variability Index (GVI) and processes data and/or provides output responsive to the GVI. The GVI can be a useful representation of the user's glucose variability over time and can consist of one or more numerical values.

In some implementations, the GVI is determined based on the length of a line or distance traveled of a host's glucose concentration over a defined period of time. That is, the GVI can be indicative of the length of the line representing the host's glucose concentration as plotted on a chart over a defined period of time. In some implementations, the length of the line may then be normalized for the defined period of time to provide a numerical value representative of the host's GVI. The following equation (1) can be used to represent the GVI:

$$GVI = L/L_o \quad (1)$$

where L is the length of the line of the user's glucose concentration over a defined duration of time and $L_o$ is an ideal length of line for the given duration.

As a non-limiting example illustrating how a GVI can be implemented using the above GVI methodology, a GVI of 1.0 can indicate no variability (is a flat line), a GVI between the range of about 1.0 and 1.2 can indicate a low variability (likely a non-diabetic), a GVI between the range of about 1.2 and 1.5 can indicate a modest variability, and a GVI greater than 1.5 can indicate a high glycemic variability.

Figure 5A:
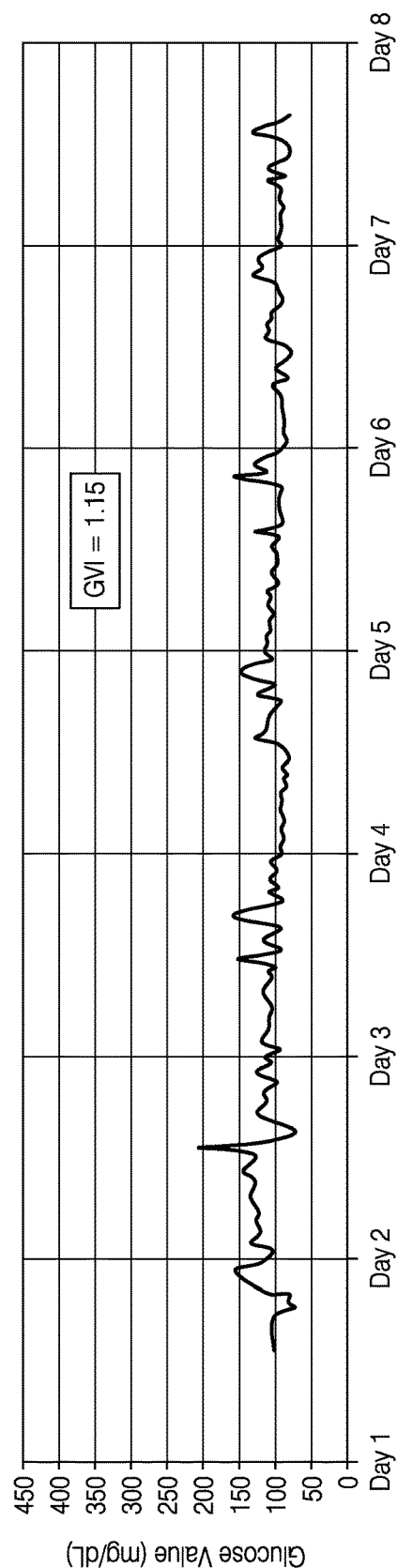
FIGS. 5A-5C are a graphs of glucose concentration data plotted over several days indicative of different levels of glucose control and associated Glucose Variability Index scores in accordance with some exemplary implementations.
Figure 5B:
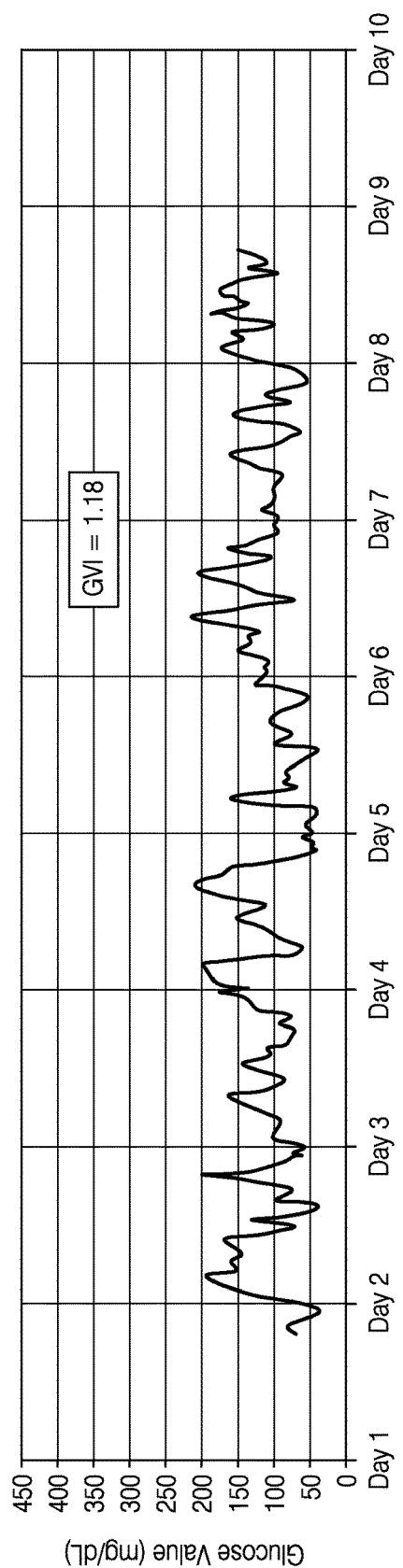
Figure 5C:
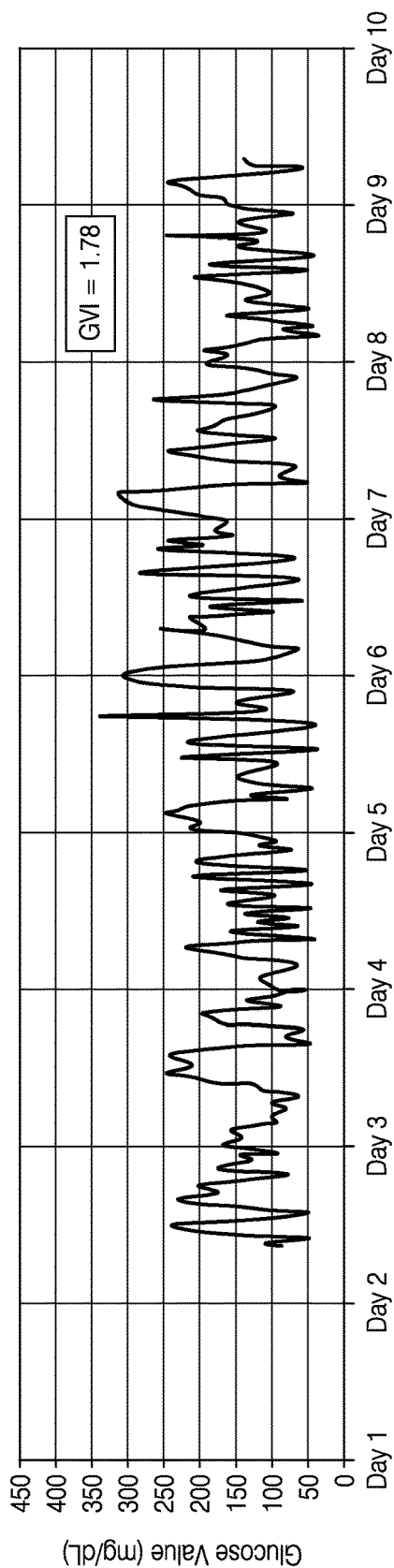

For non-limiting illustrative purposes, FIGS. 5A-5C are graphs of different glucose concentrations of a host measured by a continuous glucose monitoring system and the associated GVI score calculated using equation (1). FIG. 5A illustrates what is believed to be a very low glycemic variability, FIG. 5B illustrates what is believed to be a low glycemic variability and FIG. 5C illustrates what is believed to be a high glycemic variability.

In some implementations, the length of the line of the user's glucose concentration can be calculated using known mathematical geometrical or topographical methods. For example, in some implementations the length of the line is calculated by summing small sections of the line of the user's glucose concentration falling within the defined duration of time. In some implementations, this operation can be performed using a computer spreadsheet application, such as Excel® commercially available by Microsoft Corp.

Patient Glycemic Status

Additional indexes may be calculated based on GVI, as well. For example, some implementations calculate a Patient Glycemic Status (PGS) based on the product of the GVI, the patient's mean glucose concentration, and one minus the percentage time the host was in range during the defined period of time. Accordingly, the following equation (2) can be used:

$$PGS = GVI \times MG \times (1-PTIR) \qquad (2)$$

where MG is the mean glucose and PTIR is the percentage of time "in range." In range can be defined as a range of glucose values between which is believed to be acceptable glucose levels for the user. This range can be preset or it can be user-configured. In one implementation, in range is defined as glucose levels falling between 88 and 120 mg/dL. It is believed that the PGS can provide a good indication of a host's overall glycemic status over the defined period of time.

As a non-limiting example illustrating how a PGS can be implemented using the equation (2), a PGS less than about 30 can indicate excellent glycemic status (likely a non-diabetic), a PGS between the range of about 30 and 80 can indicate a good glycemic status, a PGS between the range of about 80 and 130 can indicate a poor glycemic status, and a PGS greater than 130 can indicate a very poor glycemic status.

While calculating PGS using equation (2) is believed to be adequate in many situations, it is believed that additionally adding a non-linear hypoglycemic penalty to equation (2) can help identify situations in which a user suffers from frequent hypoglycemic episodes. Accordingly, equation (3) can be used to calculate PGS in some implementations:

$$PGS = GVI \times MG \times (1-PTIR) + Penalty \qquad (3)$$

where the Penalty of equation (3) is a non-linear hyperbolic function that asymptotes with 5 to 7 episodes of severe hypoglycemia a week. Sever hypoglycemia can be defined using a glucose level threshold and/or a glucose level threshold and a time the user's glucose concentration spends below a glucose level threshold.

The Penalty of equation (3) can effectively double the threshold PGS values described above with respect to equation (2). Accordingly, using equation (3), a PGS less than about 60 can indicate excellent glycemic status (likely a non-diabetic), a PGS between the range of about 60 and 160 can indicate a good glycemic status, a PGS between the range of about 160 and 260 can indicate a poor glycemic status, and a PGS greater than 260 can indicate a very poor glycemic status.

In some implementations, one or both of GVI and PGS can be used to identify problems in glycemic control. A computer system can be used to automatically identify problems by comparing the GVI and/or PGS to one or more predetermined thresholds and triggering an alert responsive thereto. Further, a computer system can generate a report that indicates one or both of the GVI and PGS. The report can be viewed by the host, caretaker and/or a healthcare professional to identify problems and suggest modifications to the host's management routine to improve managing his or her condition.

Figure 6:
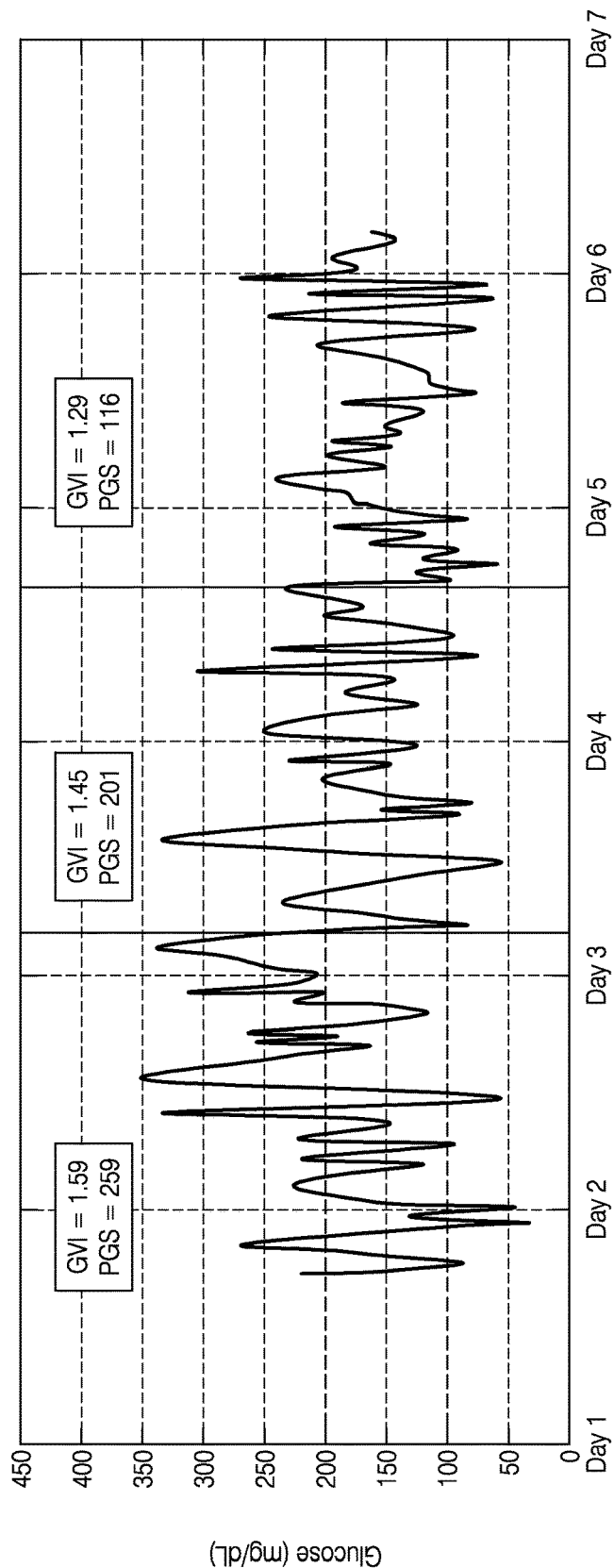
FIG. 6 is a graphs of glucose concentration data plotted over several days indicative of different levels of glucose control and associated Glucose Variability Index scores and Patient Glycemic Status scores in accordance with some exemplary implementations.

To illustrate, FIG. 6 is a graph of a user's glucose concentration over time with an indication of GVI and PGS (PGS calculated using equation (2)) for each three sections of data. The three sections illustrate different GVI and PGS scores and the associated sensor data.

Figure 7:
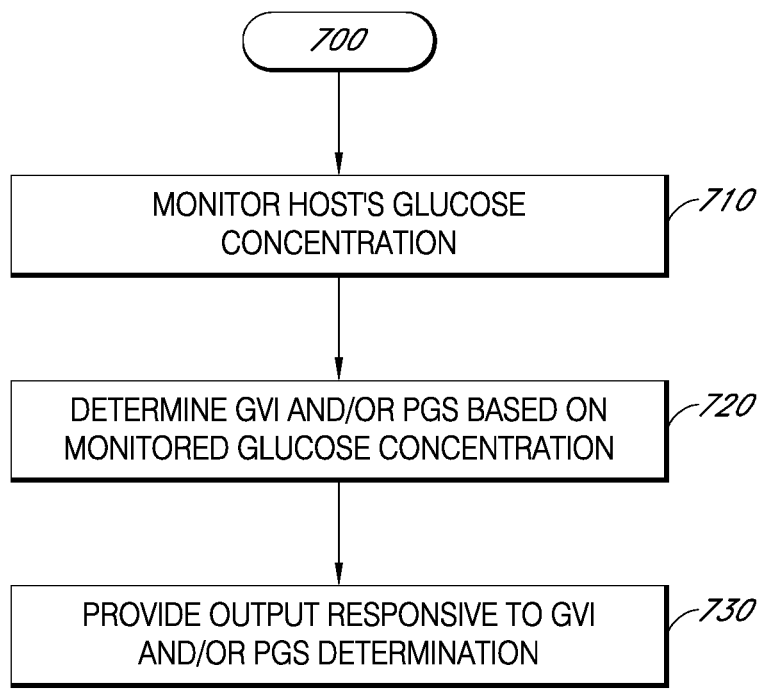
FIG. 7 is a flowchart of a glycemic variability management process in accordance with some implementations.

FIG. 7 is a flowchart of glycemic variability management process 700 in accordance with some implementations. Process 700 may be implemented using system 100 of FIG. 1. Further, instructions for implementing process 700 may be embodied as computer code stored in computer memory and executed by one or more processors of the system 100 of FIG. 1.

Further to FIG. 7, process 700 monitors a host's glucose concentration at block 710. Any of the glucose monitoring devices and systems described herein can be used to monitor the host's glucose concentration, such as the DexCom G4® Platinum continuous glucose monitoring system. Sensor electronics module 8 and/or display device 14, 16, 18, 20 can receive the sensor data generated by the sensor and process and store the sensor data. Further, the sensor data can be transmitted to cloud-based processor 490 via network for processing using process 700.

At block 720, process 700 determines a GVI and/or PGS score based on the sensor data. The GVI and PGS scores can be calculated using any of the methodologies described herein. Further, because the GVI and PGS scores can be calculated over a defined period of time in some implementations, a user may select the defined period of time using a user interface of one of devices 14, 16, 18, 20 of FIG. 1 for which the GVI and PGS scores are calculated, for example. The defined period of time can be three days, one week or one month, for example.

At block 730, process 700 provides output responsive to the GVI and/or PGS score determination. The output can be a report displayed on a user interface or printed using a printer. The report can include an indication of the GVI and/or PGS as a numerical value or using a graphic, such as a bar graph, arrow, and the like. The output can additionally or alternatively be in the form of an alert that is triggered responsive to the GVI and/or PGS exceeding one or more predetermined thresholds. The alert can be automatically sent to the host, host's caretaker or health care provider over network 406, for example.

Further, process 700 can be performed periodically or continuously in real time. That is, as new sensor data is generated, process 700 can periodically or continuously determine GVI based on the new sensor data and the past data that falls within a defined period of time. To illustrate, in one example, a new sensor data point is generated every five minutes. Process 700 may be performed wherein the defined period of time spans from the most recent data point to a defined period in the past, such as 5 hours. Process 700 can be repeated for each new data point that is received, or repeated every predetermined amount of time, such as one hour or one day.

Additionally, in some implementations, process 700 can include calculating a GVI for a plurality of different time frames. For example, a GVI may be calculated based on the past hour, the past five hours, past 24 hours, past day and past month. A user can then compare the GVI for each of the time frames to understand changes in his or her glycemic control.

Clinical Relevance Scoring

A pattern algorithm can be applied to statistical data (e.g. measured analyte values) and scored according to clinical relevance, in accordance with some embodiments. The score can then be outputted to a host or caretaker to provide a useful indication of the user's control of a health characteristic over a period of time. The following is a non-limiting example algorithm for scoring clinical relevance, where the analyte is glucose.

A scoring map is provided that coverts glucose values to a clinical relevance score. That is, the scoring map can convert glucose values in one numerical scale/units (e.g., mg/dL) to another scale/units that is based on a clinical relevance. The map can be defined algorithmically by one or more mathematical equations in some implementations. Further, in some implementations, the map projects the coordinate space of 40-400 mg/dL into two separate coordinate spaces comprising above and below a target range. The target range can be defined as an ideal glucose value for a user, such as between 110 mg/dL, although it is understood that other values can be used or that instead of a value, as range is used, such as 80-120 mg/dL. The map converts one numerical scale/units to other scale/units (e.g. from mg/dL glucose to GVI score). In some implementations, the numerical range of the clinical relevance scale is from 1.0 to 10.0 and represents the increasing clinical significance away from target, although it is understood that other scales can be used instead, such as 0.0 to 1.0 or 1 to 100.

The mapping can be non-linear in the space of glucose concentration in some implementations. For example, clinical symptoms can get somewhat exponentially worse the further a patient drifts from target. Further, the mapping can be different for above versus below target. For example, it is believed that a glucose level in humans of 50 mg/dL below a target is very different (e.g. significantly clinically more severe) than 50 mg/dL above a target range, where the target is 105 mg/dL, for example.

In some implementations, the score map in the clinical relevance scale can be linear—in contrast to the glucose concentration scale. That is, the glucose values are mapped to the clinical relevance scale so that each unit in the clinical relevance scale changes along the entire scale at approximately the same rate as the increase in clinical significance. However, in alternative implementations, the map range can be logarithmic; for example, similar to the decibels and Richter scales where every integer unit increase is ten times worse.

Every glucose value within a specified date range—if any date range is provided—can then be converted into units of clinical relevance according to the clinical relevance scoring map.

Once converted, a statistical algorithm can be applied to the values in units of clinical relevance to generate a composite clinical relevance score. The algorithm can take one or more of the sum, mean, average standard deviation, etc., of the values. For example, in some implementations, the composite score can be the mean score of all of the values within the specified date range.

The results of the mapped score can then be processed and outputted. The output can include a numerical score, such as a composite high/low mean score of all values within a specified time range, a combined mean score of all values within a specified time range, and/or one or more graphs over time of the composite and/or combined scores.

Figure 8:
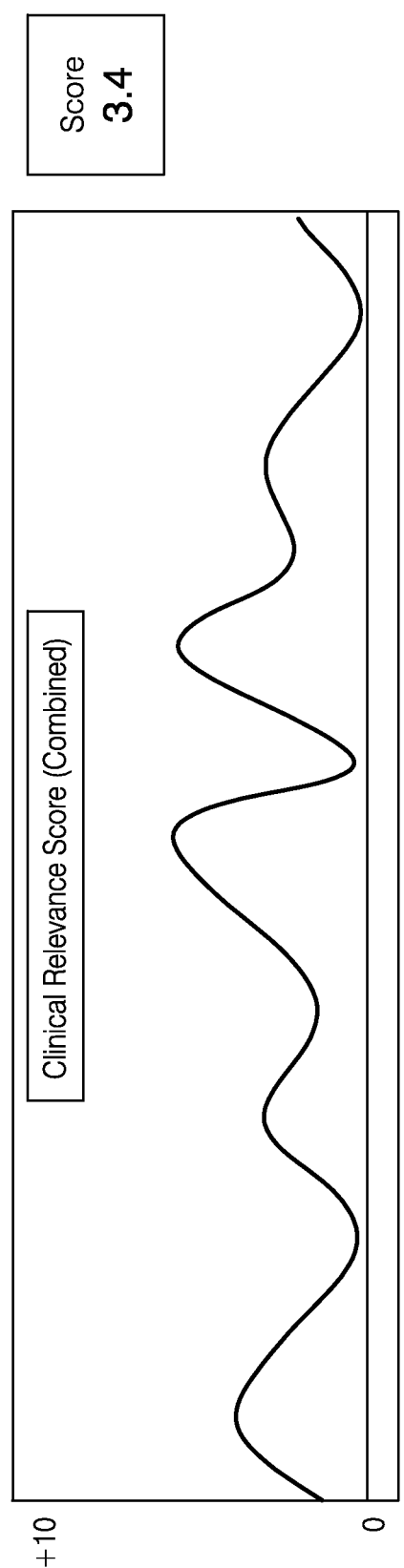
FIG. 8 is a graph of a combined Clinical Relevance score over time and a numerical combined Clinical Relevance score value in accordance with some implementations.

FIG. 8 is a graphical representation of a combined score output displayed on a user interface of device 14, 16, 18, 20 in accordance with some implementations. Here, the score is on a scale of 1 to 10 along the y-axis over time on the x-axis. A numerical score that is the mean of the scores illustrated in the graph is displayed to the right of the graph.

Figure 9:
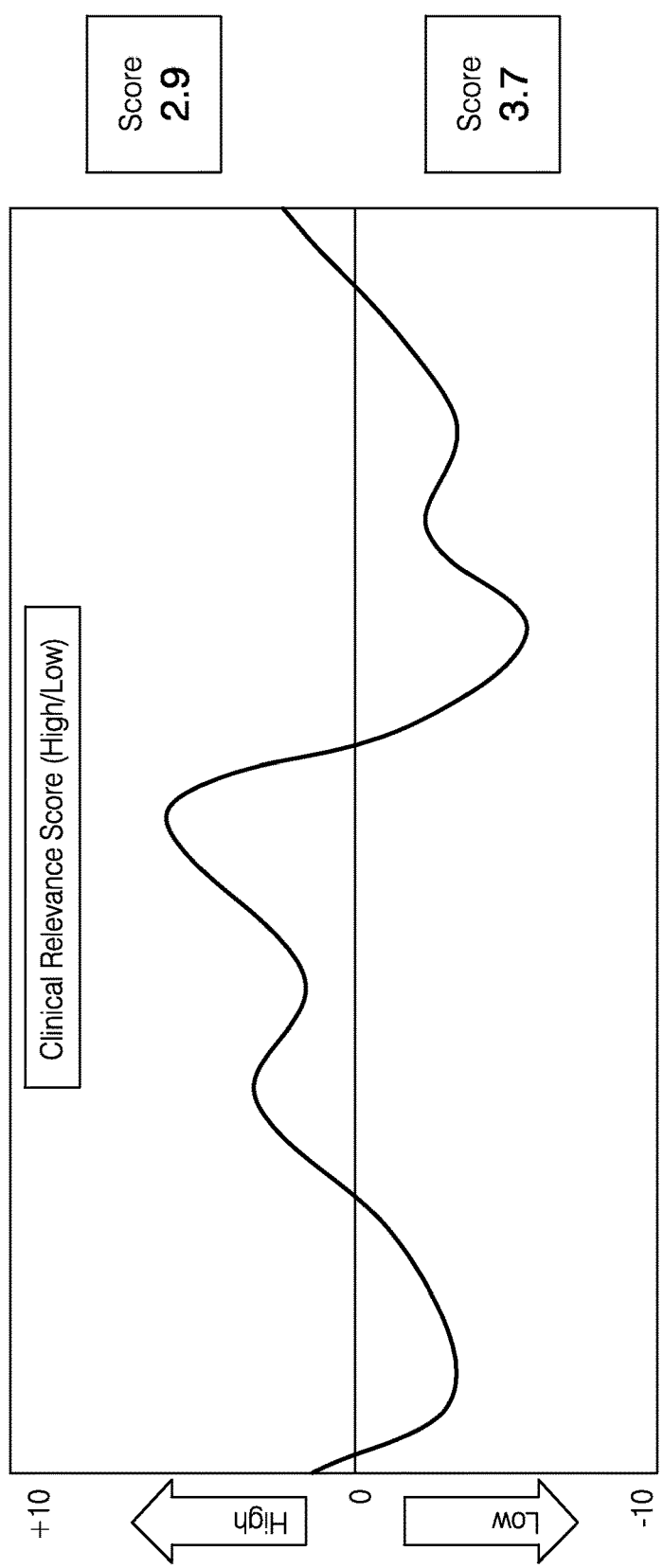
FIG. 9 is a graph of a composite high/low Clinical Relevance scores over time and numerical composite high/low Clinical Relevance score values in accordance with some implementations.

FIG. 9 is a graphical representation of a composite score output displayed on a user interface of device 14, 16, 18, 20 in accordance with some implementations. Here, the graph provides clinical relevance away from target in both high and low directions. Further, separate high and low numerical scores representative of the mean of all high scores and all low scores, respectively, are provided on to the right of the graph.

In some implementations, scores can also be bucketed into five minute epochs over a modal day for any number of days desired. From this sum or average for each epoch can be obtained and plotted over a day.

In some implementations, the map is designed so that scores range from 0 to 10. A 0 score can indicate very good glycemic variability, and a 10 score can indicate very poor glycemic variability.

In some implementations, the score is normalized to have equivalent clinical relevance for high and low blood glucose ranges. For example, a score of 6.5 for a high only blood glucose reading has and equivalent clinical relevance of a score of 6.5 for a low only blood glucose reading. Likewise, a score for a composite/combined blood glucose reading has the same meaning as a score of 6.5 for both high low and low only blood glucose readings.

Retrospective Analysis of Real-Time Generated Analyte Data

In some implementations, system 100 can re-analyze real-time measured analyte data retrospectively to provide greater insight in managing a health condition, such as retrospectively analyzing glucose data to manage diabetes.

A non-limiting example is a patient with type-2 diabetes going through basal insulin titration. In the morning, the patient may need to decide whether to increase, decrease, or maintain insulin rates. The patent can use system 100, which includes a continuous glucose monitor, such as the Dexcom G4® Platinum continuous glucose monitoring system and initiates a re-analysis of historical glucose information, such as the past days', weeks' or months' glucose information. The initiation can be performed by a user selecting a menu item displayed on a user interface of one or more of display device 14, 16, 18 20, for example. The system 100 reanalyzes the historical glucose information and changes any historical trend information to reflect greater accuracy from a retrospective analysis of the data. The retrospectively analyzed data can be used by the patient to adjust his or her basal insulin administration protocols.

Further, the retrospectively analyzed data can be further processed to identify possible events and provide event markers on a glucose trend graph for a user to visualize. For example, if the user's glucose drops every Tuesday at 10 am in a consistent pattern, a retrospective analysis can prompt the user to ask whether he exercises during that time period and store the user's answer to the prompt.

System 100 can also programically analyze data after a predetermined amount of time, such as at the end of each day, and provide a message to the user with information based on the data analysis. For instance, a push notification, or local notification, can be automatically displayed on the user interface of device 14, 16, 18, 20 at predetermined times with the percentage of glucose values that were within a specified glucose range that day. It is believed that doing so can provide motivation to the user to maintain his or her glucose levels within the specified range.

Automatic Detection of Missed Insulin Administration

System 100 can also be used to detect missed insulin and provide a timely notification to the patient/user for the prevention of hyperglycemia, in accordance with some implementations. It is believed that high positive rates of change (3-8 mg/dL/min) occur infrequently and are almost always associated with missed insulin administration. When sustained high positive rates of change are detected (e.g., 3-8 mg/dL/min over 10-15 minutes duration) with system 100, a specific alarm can be provided on display 14, 16, 18, 20 alerting the user to the possibility that they may have missed an insulin administration. This could occur as a result of inattention or distraction, e.g. a "missed meal bolus". In insulin pump therapy, missed meal boluses often occur when the patient/user sets the bolus amount but forgets to apply the final confirmation necessary to initiate delivery of insulin. Similarly, patients administering insulin by injection can also forget to give insulin at mealtime to cover the carbohydrate content of a meal. However, missed insulin can also occur as a result of an insulin pump failure, e.g., an occlusion in the insulin tubing or cannula. Finally, missed insulin can occur as well in situations in which a patient/user assumes that he/she has been given a "diet" drink (e.g., cola, lemonade etc.), but due to error, has been given a high carbohydrate content beverage instead. Under these circumstances, the patient/user would typically not give insulin and then experience a rapid rise in glucose due to the error.

Pattern Detection on Troublesome Meals

System 100 can be used to make event entry and download for reports more useful to the patient, physician, nurse, educator and dietician, in accordance with some implementations.

Calculating bolus insulin for mealtime is often complicated to a user. One difficulty can be estimating the number of carbohydrates in a meal. If the estimation by the patient is inaccurate, the corresponding insulin dose will be off which may result in hypo or hyperglycemia. When patients retrospectively analyze his or her data, for example, it can be difficult to now review a problem meal and draw any useful insights given the data that is available with just carbohydrate logging. For instance, a patient may ask themselves "What was the meal?", "Were the carbs estimated correct?", "Was the glycemic index different?", "Did I take my insulin too early or too late?", "Did I inject the correct amount of insulin?"

Most people only eat 12-15 different meals. By having system 100 look for problems by specific meal (e.g. carne asada burrito vs. 2 slices of pizza) system 100 can programically highlight meals that have a pattern of poor control and give an insight to the user that they may be mis-estimating the number of carbs in a given meal. This data becomes actionable. The following is an exemplary implementation that may be programically implemented using system 100.

Part 1: Meal events. Rather than having event entry input the number if carbs for each meal and have the user estimate carbs every meal, have a list of meals to choose from. Typical users only eat 12-20 different meals most of the time. The selection can start with breakfast1, breakfast2, lunch1, lunch2, etc. and allow the user to name the meal more specifically on display device 20 and download that information to another display device, such as display device 16, which would change the meal. Each meal would have information relevant to the meal such as carbohydrates, glycemic index, etc. stored under that meal. The user when logging a meal simply selects the meal they ate.

Part 2: Meal event setup. Meal setup can be done any of display device 14, 16, 18, 20. If device 14, 16, 18, 20 has access to the Internet, the setup problem can be connected to a food database that can allow the user to select a common meal and download accurate information about the meal reducing the need for carb counting. The user can setup a list of 10, 20 or more common meals they eat frequently which configures a menu on the receiver with the meal name.

Part 3: Pattern analysis. The analysis software in system 100 determines poor control around specific meals and reports issues relating to them providing insight to the user that they may be misestimating or mistiming meal insulin bolus by providing an alert to the user using user interface of device 14, 16, 18, 20.

Pattern Recognition of Glucose Trends Based on Location and Duration of Insulin Pump Infusion Site Wear Some implementations of system 100 programically provide information to a user about how sites and duration of wear of insulin infusion pumps influence glucose control of the user. Here, system 100 can prompt a user about the location of an insulin infusion site upon priming the insulin pump for use, for example. The system 100 can then track the duration of the use of the insulin pump. Upon a request from the user, the system 100 can programically analyze the user's glucose readings using a continuous glucose sensor worn by the patient over the time period that the insulin pump was worn and provide output to the user as to the user's glucose control. The user can then use this information to determine if certain locations and/or durations of wearing the insulin pump may provide different levels of glucose control in the user. The information may also be transmitted to a medicament delivery device such as a pump or pen for automated control of insulin from the medicament delivery device based at least in part on the information.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs))

used to provide machine instructions and/or data to a programmable processor, including a machine-readable medium that receives machine instructions.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. As used herein, the term "based on" also refers to "based on at least." Other implementations may be within the scope of the following claims.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,559; 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-

0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No.

2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; and U.S. Patent Publication No. 2005-0182451-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; and U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS".

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A computer-implemented method for improving glucose management for a patient by reducing glycemic variability, the method comprising:
   receiving input indicative of one or more insulin infusion sites on the patient including one or more of a location on a body for the one or more insulin infusion sites and a duration of use of an insulin delivery device;
   generating, using one or more continuous glucose sensors, continuous glucose sensor data indicative of a glucose concentration of the patient;
   based on the continuous glucose sensor data, determining one or more glucose control metrics for each of the one or more insulin infusion sites;
   comparing the determined one or more glucose control metrics to a predetermined threshold;
   identifying, based on the comparing, a problem associated with at least one of the location or the duration of use of the insulin delivery device;
   determining a suggestion for modifying a glucose management routine based on the identified problem;
   outputting information to a user based on the determined one or more glucose control metrics for each of the one or more insulin infusion sites, the outputted information including the identified problem and the determined suggestion; and
   controlling insulin delivery by the insulin delivery device to reduce glycemic variability using at least one of the identified problem or the determined suggestion for modifying the glucose management routine.

2. The method of claim 1, further comprising prompting, using a user interface, for information indicative of the one or more of the location and the duration of use.

3. The method of claim 1, wherein the one or more insulin infusion sites comprises a plurality of insulin infusion sites.

4. The method of claim 1, further comprising determining a timeframe associated with use of at least one of the one or more insulin infusion sites based on the duration of use, wherein determining the one or more glucose control metrics is based on glucose sensor data indicative of the patient's glucose concentration within the timeframe.

5. The method of claim 1, wherein outputting information comprises providing via a user interface an indication of glucose control associated with each of a plurality of different insulin infusion sites.

6. The method of claim 1, wherein the one or more glucose control metrics is indicative of the patient's glucose control relative to a glucose target value or range over time.

7. A system for improving glucose management for a patient by reducing glycemic variability, the system comprising:
   one or more continuous glucose sensors configured to generate continuous glucose sensor data indicative of a glucose concentration of the patient;
   at least one processor; and
   at least one memory including code which when executed by the at least one processor provides operations comprising:
      receiving input indicative of one or more insulin infusion sites on the patient and including one or more of a location on a body for the one or more insulin infusion sites and a duration of use of an insulin delivery device,
      based on the continuous glucose sensor data, determining one or more glucose control metrics for each of the one or more insulin infusion sites,
      comparing the determined one or more glucose control metrics to a predetermined threshold,
      identifying, based on the comparing, a problem associated with at least one of the location or the duration of use of the insulin delivery device,
      determining a suggestion for modifying a glucose management routine based on the identified problem,
      outputting information to a user based on the determined one or more glucose control metrics for each of the one or more insulin infusion sites, the outputted information including the identified problem and the determined suggestion, and
      controlling insulin delivery by the insulin delivery device to reduce glycemic variability using at least one of the identified problem or the determined suggestion for modifying the patient's glucose management routine data.

8. The system of claim 7, wherein the operations further comprise prompting, using a user interface, for information indicative of the one or more of the location and the duration of use.

9. The system of claim 7, wherein the one or more insulin infusion sites comprises a plurality of insulin infusion sites and where one or more glucose control metrics is determined for each of the plurality of insulin infusion sites.

10. The system of claim 7, wherein the operations further comprise determining a timeframe associated with use of at least one of the one or more insulin infusion sites, wherein determining the one or more glucose control metrics is based on glucose sensor data within the timeframe.

11. The system of claim 7, wherein outputting information comprises providing via a user interface of the system an indication of glucose control associated with each of a plurality of different insulininfusion sites.

12. The system of claim 7, wherein the one or more glucose control metrics is indicative of the patient's glucose concentration over time relative to a glucose target value or range.

13. The method of claim 1, wherein identifying the problem includes automatically detecting missed insulin administration by analyzing the continuous glucose sensor data.

14. The method of claim 1, further comprising receiving a user-selection of meals from a list of meals available for selection and associating the continuous glucose sensor data to the user selection of meals, wherein: identifying the problem includes detecting one or meals associated with poor glucose control by analyzing the continuous glucose sensor data for glucose control patterns for the user-selection of meals.

15. The method of claim 14, wherein determining the suggestion includes suggesting different timing or dosing for insulin infusion for the one or more meals associated with poor glucose control.

16. The method of claim 1, wherein identifying the problem includes analyzing the continuous glucose sensor data to detect glucose control patterns for the location or the duration, and determining the suggestion includes determining a suggestion for a location change for insulin infusion or a duration change for using the insulin delivery device.

17. The method of claim 1, wherein determining one or more glucose control metrics includes determining a glycemic variability index representing glucose variability over time.

18. The method of claim 17, wherein determining the glycemic variability index includes determining a length of a line representing glucose concentration over time.

19. A method for improving glucose management for a patient by reducing glycemic variability, the method comprising:
   receiving input indicative of one or more insulin infusion sites on the patient, wherein the received input includes input indicative of a location on a body for the one or more insulin infusion sites, a duration of use of an insulin delivery device, or both the location on the body and the duration of use of the insulin delivery device;
   generating, using one or more continuous glucose sensors, continuous glucose sensor data indicative of a glucose concentration of the patient;
   for each of the one or more insulin infusion sites, determining a glucose variability index based on the continuous glucose sensor data;
   comparing the glucose variability index to a predetermined threshold;
   identifying, based on the comparing, a problem associated with at least one of the location or the duration of use of the insulin delivery device;
   determining a suggestion for modifying a glucose management routine based on the identified problem; and
   based on the glucose variability index for each of the one or more insulin infusion sites, outputting to a user the identified problem and the determined suggestion for use in reducing glycemic variability by modifying the glucose management routine including insulin delivery.

20. The method of claim 19, further comprising controlling insulin delivery by an insulin delivery device using at least one of the identified problem or the determined suggestion.

* * * * *

UNITED STATES PATENT AND TRADEMARK OFFICE
CERTIFICATE OF CORRECTION

PATENT NO. : 10,369,283 B2  
APPLICATION NO. : 14/065847  
DATED : August 6, 2019  
INVENTOR(S) : Naresh C. Bhavaraju et al.

Page 1 of 1

It is certified that error appears in the above-identified patent and that said Letters Patent is hereby corrected as shown below:

On the Title Page

In Column 2 (item (56)) at Line 12, Under Other Publications, change "GluCulator:" to --GlyCulator:--.

In Column 2 (page 2, item (56)) at Line 18, Under Other Publications, change "glucemic" to --glycemic--.

In the Specification

In Column 15 at Line 3, Change "programically" to --programmatically--.

In Column 15 at Lines 60-61, Change "programically" to --programmatically--.

In Column 15 at Line 65, Change "programically" to --programmatically--.

In Column 16 at Line 27, Change "programically" to --programmatically--.

In Column 16 at Line 34, Change "programically" to --programmatically--.

In the Claims

In Column 27 at Line 47, In Claim 7, change "routine data." to --routine.--.

In Column 27 at Line 64, In Claim 11, change "insulininfusion" to --insulin infusion--.

In Column 28 at Line 12, In Claim 14, after "or" insert --more--.

Signed and Sealed this  
Twelfth Day of November, 2019

Andrei Iancu  
*Director of the United States Patent and Trademark Office*